United States Patent
Stopek et al.

(10) Patent No.: US 9,572,596 B2
(45) Date of Patent: Feb. 21, 2017

(54) APPLICATORS FOR CONTROLLED IN SITU DELIVERY OF THERAPEUTIC COMPOSITIONS AND IMPLANTS, METHODS OF FABRICATION AND USE

(75) Inventors: Joshua Stopek, Guilford, CT (US); Michael Minette, New Haven, CT (US)

(73) Assignee: Covidien LP, Mansfield (*) Notice: Subject to any disclaimer, the term of this patent is extended or adjusted under 35 U.S.C. 154(b) by 672 days.

(21) Appl. No.: 13/539,516

(22) Filed: Jul. 2, 2012

(65) Prior Publication Data

US 2013/0006169 A1 Jan. 3, 2013

Related U.S. Application Data

(60) Provisional application No. 61/502,886, filed on Jun. 30, 2011.

(51) Int. Cl.
| | |
|---|---|
| A61B 17/34 | (2006.01) |
| A61M 11/06 | (2006.01) |
| A61M 13/00 | (2006.01) |
| A61M 11/00 | (2006.01) |

(52) U.S. Cl.
CPC ......... *A61B 17/3474* (2013.01); *A61M 11/005* (2013.01); *A61M 11/06* (2013.01); *A61M 13/00* (2013.01)

(58) Field of Classification Search
CPC ................ A61M 15/009; A61M 2205/3334; A61M 11/005; A61M 11/06; A61M 13/00; A61B 17/3474
USPC .................. 604/24, 25, 70, 98.01, 141, 140, 146, 604/147; 128/200.14, 200.16
See application file for complete search history.

(56) References Cited

U.S. PATENT DOCUMENTS

| | | | |
|---|---|---|---|
| 1,354,641 A * | 10/1920 | Zietlow ................... | B05B 11/06 128/200.14 |
| 5,098,775 A * | 3/1992 | Harada ................... | A61F 13/534 442/261 |
| 5,164,740 A | 11/1992 | Ivri | |
| 5,246,419 A | 9/1993 | Absten | |
| 5,586,550 A | 12/1996 | Ivri et al. | |
| 5,758,637 A | 6/1998 | Ivri et al. | |
| 5,938,117 A | 8/1999 | Ivri | |
| 6,014,970 A | 1/2000 | Ivri et al. | |
| 6,085,740 A | 7/2000 | Ivri et al. | |
| 6,461,361 B1 * | 10/2002 | Epstein ............ | A61B 17/00491 222/145.2 |
| 6,540,154 B1 | 4/2003 | Ivri et al. | |
| 6,546,927 B2 | 4/2003 | Litherland et al. | |
| 6,845,770 B2 | 1/2005 | Klimowicz et al. | |
| 2005/0021766 A1 | 1/2005 | McKeowen et al. | |
| 2005/0247305 A1 * | 11/2005 | Zierenberg ........ | A61M 15/0065 128/200.14 |
| 2006/0151629 A1 * | 7/2006 | Vedrine ................. | A61M 11/06 239/329 |
| 2007/0044793 A1 * | 3/2007 | Kleinstreuer ....... | A61M 16/208 128/200.21 |

(Continued)

FOREIGN PATENT DOCUMENTS

| | | |
|---|---|---|
| WO | WO 2004/043274 A1 | 5/2004 |
| WO | WO 2005/092264 A1 | 10/2005 |
| WO | WO 2008/117264 A1 | 10/2008 |

*Primary Examiner* — Emily Schmidt
*Assistant Examiner* — Lauren M Peng

(57) ABSTRACT

The present disclosure relates to applicators designed for controlled in situ delivery of therapeutic films or depots during a surgical procedure.

20 Claims, 6 Drawing Sheets

(56) References Cited

U.S. PATENT DOCUMENTS

| | | |
|---|---|---|
| 2007/0105972 A1* | 5/2007 | Doyle ................ B81C 99/0095 522/1 |
| 2009/0192444 A1 | 7/2009 | Albrecht et al. |
| 2010/0247932 A1* | 9/2010 | Jinks ................... A61M 15/009 428/447 |
| 2011/0030678 A1* | 2/2011 | Power ................ A61B 17/3421 128/200.14 |
| 2011/0230820 A1 | 9/2011 | Lillis et al. |
| 2012/0022495 A1* | 1/2012 | Sargeant et al. ............. 604/500 |
| 2012/0209166 A1 | 8/2012 | Power et al. |

* cited by examiner

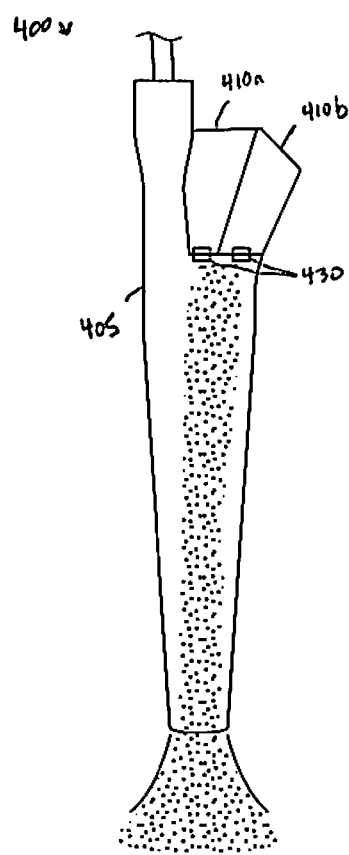
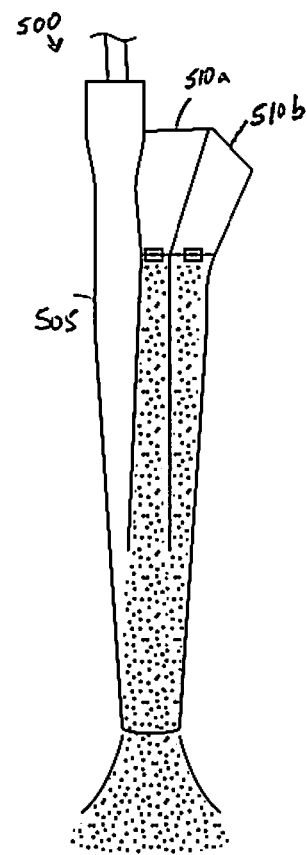
FIG. 4      FIG. 5

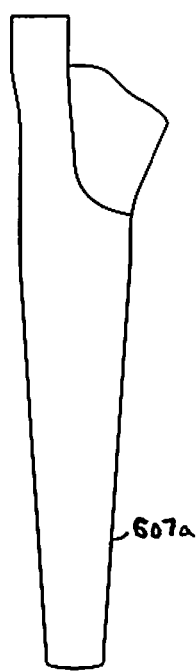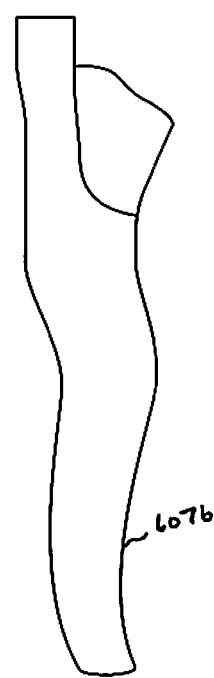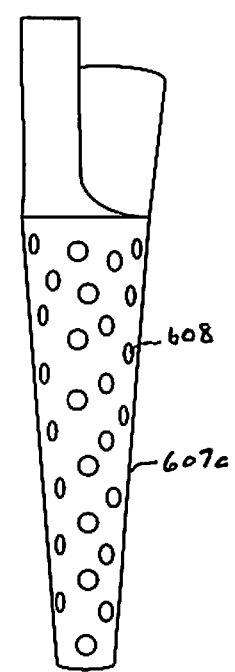
FIG. 6A  FIG. 6B  FIG. 6C

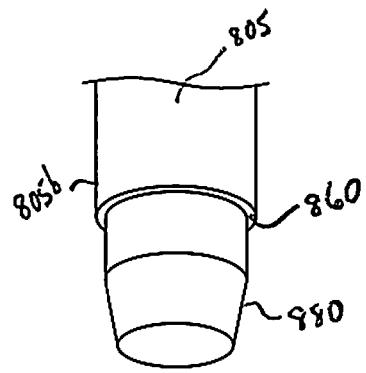
FIG. 8
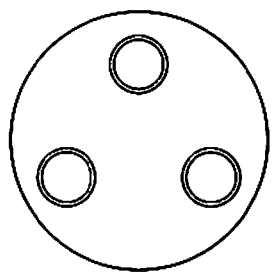
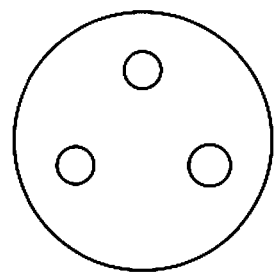
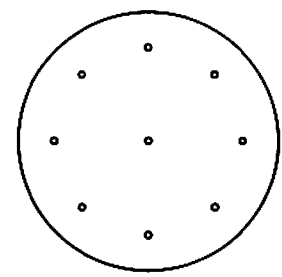
FIG. 8A     FIG. 8B     FIG. 8C

APPLICATORS FOR CONTROLLED IN SITU DELIVERY OF THERAPEUTIC COMPOSITIONS AND IMPLANTS, METHODS OF FABRICATION AND USE

CROSS-REFERENCE TO RELATED APPLICATION

The present application claims the benefit of and priority to U.S. Provisional Application Ser. No. 61/502,886, filed on Jun. 30, 2011, the entire disclosure of which is incorporated herein by reference.

BACKGROUND

Technical Field

The present disclosure relates generally to applicators for use in surgical procedures, and more particularly, to applicators for use in surgical procedures to control and/or sustain the delivery of at least one therapeutic agent for extended efficacy.

Background of Related Art

Laparoscopic surgical insufflation systems allowing the use of trocar-enabled aerosolizing technologies have been disclosed by others (Power et al.; US 2011/0030678), and specifically as mechanical devices which may allow the passage/delivery of a fluid/therapeutic agent to a surgical site or body cavity (i.e. standard of care anesthetics, analgesics, etc. and in place of local injection/infusion). However, little has been reported in terms of means of extending the efficacy of such therapeutic agents, or preferred materials compositions or alternative uses, and/or methods of use outside of laparoscopic approaches.

As such, these inventions and related devices leave much room for improvement pertaining to controlling and sustaining therapeutic agent delivery (for preferably extending efficacy), as well as allowing both laparoscopic and open surgical use, given the majority of reported acute postoperative pain is associated with open approaches.

SUMMARY

Accordingly, the present disclosure relates to an applicator for use in surgical procedures to control and/or sustain the delivery of therapeutic agents for extended efficacy. The applicator is designed for the localized delivery of implantable materials in situ or during surgery to form therapeutic films capable of controlling and/or sustaining delivery of therapeutic agents for extended efficacy. Unlike simply delivering therapeutic agents in an aerosolized solution or buffer, the applicator described herein is capable of delivering mixtures, as one composition and/or mixing multiple components separately in a spray field, which include therapeutic agents, biocompatible carrier materials, and solvents in situ and/or during surgery to form implantable films or therapeutic depots in any pattern, dimension, configuration deemed necessary by the medical personnel performing the surgery.

Methods of forming such therapeutic films and uses of such films are also disclosed

BRIEF DESCRIPTION OF THE DRAWINGS

The foregoing objects and advantages of the disclosure will become more apparent from the reading of the following description in connection with the accompanying drawings, in which:

FIG. 4 is a side view of an applicator according to at least one embodiment described in the present disclosure;

FIG. 5 is a side view of an applicator according to at least one embodiment described in the present disclosure;

FIGS. 6A-6C are a side view of an applicator including a variety of different distal ends according to at least one embodiment described in the present disclosure;

FIGS. 8-8C are a side view of an adjustable spray tip positioned on a distal end of an applicator according to at least one embodiment described in the present disclosure.

DETAILED DESCRIPTION

The present disclosure relates generally to an applicator for use in surgical procedures, and more particularly, to an applicator for use in surgical procedures to control and/or sustain the delivery of therapeutic agents for extended efficacy.

The applicator includes the ability to localize and/or focus the aerosolized spray mixture to very specific areas within the surgical field inside the body to form therapeutic depots and/or films directly to the tissue and/or on an implantable medical device positioned within the surgical field. The therapeutic depot and/or film formed may be a single layer or multilayer implant which may accommodate a high payload of the therapeutic agent, as compared to prepared films cast outside the body via extrusion, molding and the like. In addition, the ability to add layers in situ provides the medical personnel the ability to control and/or sustain and/or delay the release of the therapeutic agent at certain points within the tissue or surgical field. For example, the applicator may include a special tip and/or a directional cone which extends from the opening wherein the mixtures exit the applicator, thus providing the applicator with the ability to focus the spray to a specific portion of the tissue or implanted device. In another example, and/or in combination with the special tip and cone embodiments, portions of the surgical field may be lined with at least one mask made of an inert substance, such as silicone, to protect the portions of the surgical field from coming in contact with the aerosolized composition. In embodiments, the mask may also be used to act as a mold or screen for collecting the aerosolized composition into a predetermined configuration, contour, and/or shape.

Figure 1:
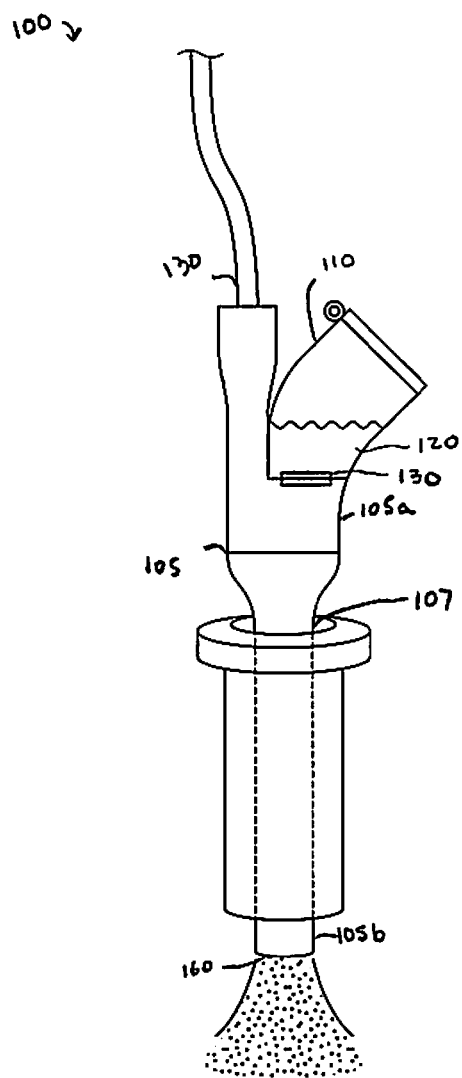
FIG. 1 is a side view of an applicator according to at least one embodiment described in the present disclosure.
Figure 2:
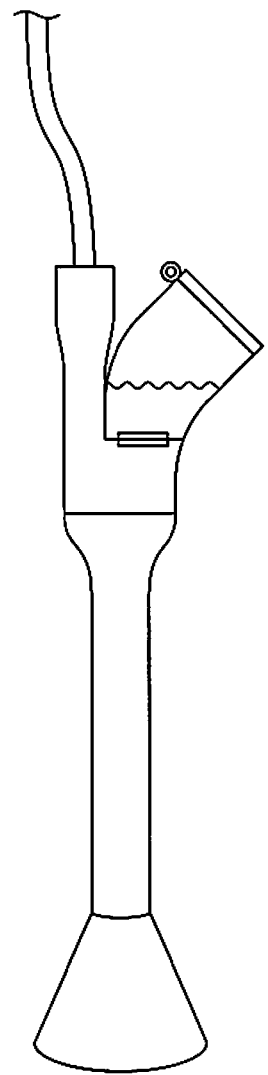
FIG. 2 is a side view of an applicator according to at least one embodiment described in the present disclosure.

Applicators for dispensing a solution as a spray are known, as are applicators for mixing two or more components to form a solution prior to dispensing the solution. With reference to FIG. 1, an applicator 100 according to an embodiment of the present disclosure is shown. The applicator 100 includes a base 105 configured for operable engagement by a user, a reservoir 110 containing a solution 120 and a mechanism 130 for aerosolizing the solution 120. As shown in FIG. 1, the applicator 100 is configured for endoscopic or laparoscopic use, i.e., through a trocar, incision or natural body orifice, or instead, may be modified for use in open procedures (FIG. 2).

With reference still to FIG. 1, the base 105 includes proximal and distal ends 105a, 105b and defines an elongated passage 107 extending therebetween. The proximal end of the base 105a is configured for operable engagement with a source of air 130. It is envisioned that the air supplied by the source of air may be heated. The distal end of the base 105b includes an elongated extension defining an outlet 160 configured for directing and dispensing the contents of the reservoir as an aerosol.

As noted above, the base includes a mechanism for aerosolizing the content of the reservoir. In one example, the aerosolizing mechanism includes an aerosol generator or nebulizer. The nebulizer facilitates the suspension of the contents of the reservoir in the air as the air from the air supply passes through the elongated passage of the base. In some instances, nebulizers may utilize a vibrating member to aerosolize the contents of the reservoir. In embodiments, the base may include a rigid material. In embodiments, the base may include a flexible material.

Figure 3A:
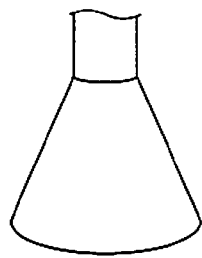
FIGS. 3A-3F are a side view of a distal end of an applicator including a cone or skirt according to at least one embodiment described in the present disclosure.
Figure 3B:
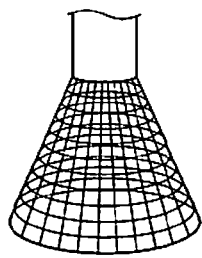
Figure 3C:
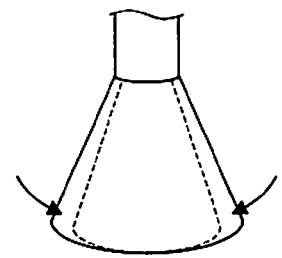
Figure 3D:
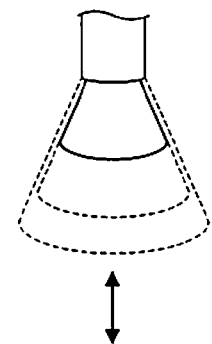
Figure 3E:
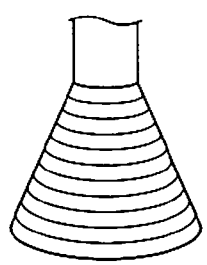
Figure 3F:
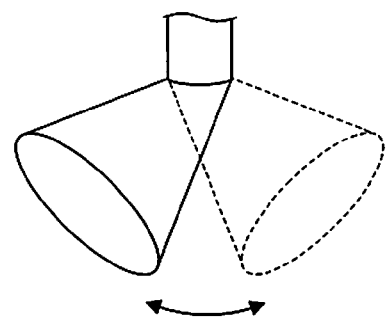

With reference to FIGS. 3A-3F, the applicator may include an attachment secured to the distal end of the base to shield and/or direct the spray dispensed from the base. As seen in FIGS. 3A-3F, the attachment includes a skirt or cone positioned on a distal end of the elongated extension adjacent the outlet. The cones and skirts may be flexible or rigid, open/porous/woven or completely closed, opaque, colored, optically clear or translucent. In one embodiment, the skirt may have a form of illumination to improve visibility in the spray region. With reference to FIG. 3A, in one embodiment, the skirt is solid and may be composed of an elastomeric material, i.e., silicone. With reference to FIG. 3B, in another embodiment, the skirt is mesh-like, i.e., woven/textile, and may be able to absorb or wick away excess spray. In alternative embodiments, the skirt may be adjustable, i.e., selectively extendable diameter (FIG. 3C), selectively retractable (FIG. 3D), selectively repositionable (FIG. 3E) and/or selectively rotatable (FIG. 3F).

With reference now to FIGS. 4 and 5, in alternative embodiments, the applicator 400, 500, respectively, may include two or more reservoirs 410, 510 and the base 405, 505 may be configured for mixing the contents of the two or more reservoirs. Referring initially to FIG. 4, the applicator 400 includes a first reservoir 410a and a second reservoir 410b. The contents of each the first and second reservoirs 410a, 410b are suspending in the air by the nebulizer 430 and the resulting aerosol is mixed prior to being dispensed. The mixing of the contents of the first and second reservoirs occurs as the aerosolized contents of the reservoirs travel through the elongated extension. The elongated extension may be configured to facilitate the mixing of the aerosolized contents, i.e., contoured surfaces. Additionally, and/or alternatively, the elongated extension may include one or more mechanisms for facilitating the mixing of the contents, i.e., spindle, rotor.

With reference now to FIG. 5, in another embodiment, the contents of the first and second reservoirs 510a, 510b are aerosolized and remain separate until immediately prior to or upon being dispensed from the elongated extension. In this manner, the contents of the first and second components may be mixed external of the base.

Referring now to FIGS. 6A-6C, the elongated extension of the base may be configured for use in various procedures. Referring initially to FIG. 6A, the elongated extension 607a is rigid. With reference to FIG. 6B, the elongated extension 607b is flexible and may be composed of silicone, urethane or any other suitable material. The flexible extension may be of any length and may include a wire or other stabilizing device for maintaining a flexed shape in the extension. Referring now to FIG. 6C, the elongated extension 607c may define one or more holes 608 along the length thereof extending radially outward therefrom. In this manner, the applicator is configured to spray laterally and may be configured to spray in a three-hundred and sixty degree (360°) pattern. It is envisioned that the elongated extension may include an aerosolize device for aerosolizing the contents of the one or more reservoir as the contents flow through the elongated passage or immediately prior to being dispensed through the outlet in the elongated extension.

Figure 7:
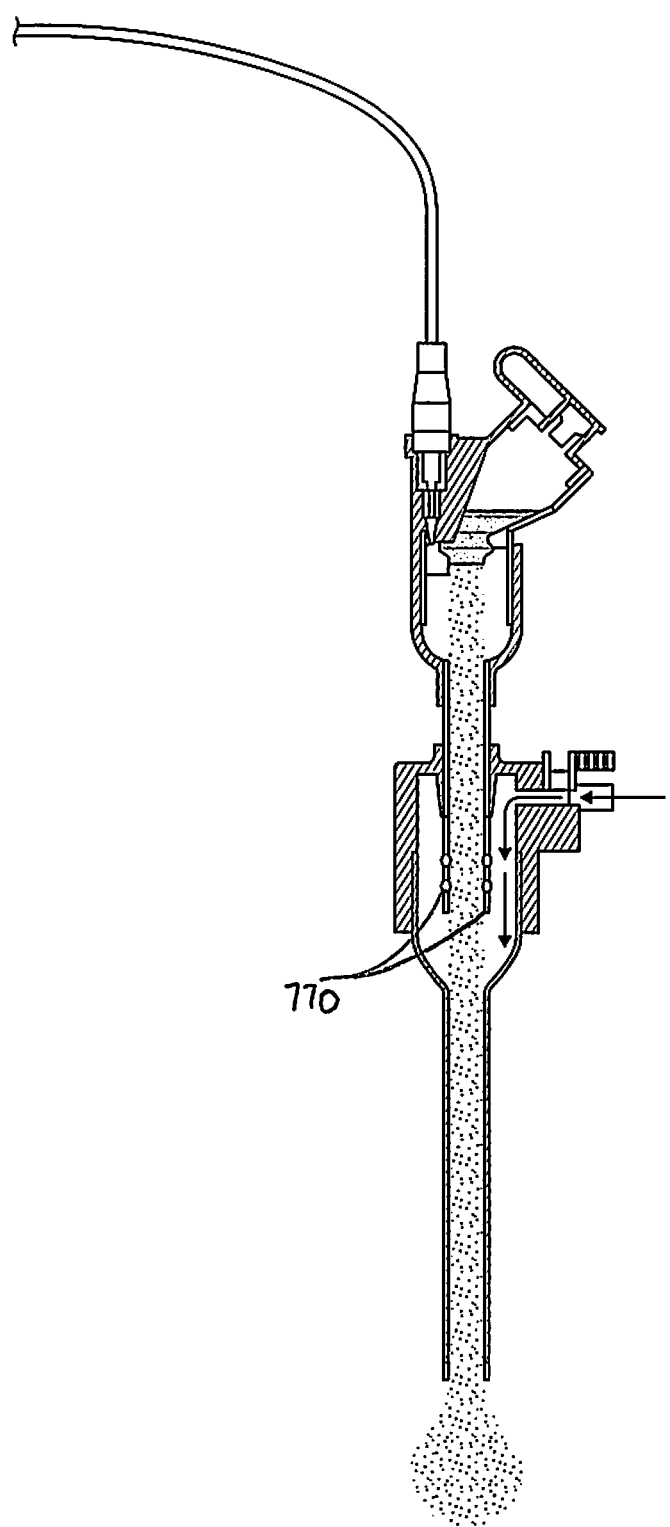
FIG. 7 is a cross-sectional view of an applicator according to at least one embodiment described in the present disclosure.

With reference now to FIG. 7, yet another embodiment of an applicator according to the present disclosure is shown. The applicator is substantially similar to the applicator disclosed in the '678 application, and will only be described as relates to the differences therebetween. One or more polymerizing members 770 are positioned along the length of the elongated passage of the base of the applicator. The polymerizing members 770 are configured to facilitate the polymerization of the aerosolized contents of the reservoir as the contents pass through the elongated passage of the base and prior to being dispensed through the outlet in the elongated extension. The polymerizing members 770 may include ultraviolet or infrared light emitting diodes, bulbs or tubes, microwave generators, any other suitable member capable of polymerizing the aerosolized solution, and a combination thereof. Although shown in an applicator having only a single reservoir, one or more polymerizing members may be incorporated into any of the presently disclosed applicator assemblies.

Referring now to FIGS. 8-8C, in one embodiment, the outlet 860 on the distal end 805b of the base 805 through which the aerosolized content of the one or more reservoirs are dispensed includes an adjustable tip 880. The adjustable tip 880 permits the varying of the spray pattern emanating from the outlet of the elongated extension. It is envisioned that the spray pattern may be adjusted prior to and/or during spraying. The adjustable tip 880 may include a configuration that forms a spray pattern having one or more large streams (FIG. 8A), one or more slightly smaller streams (FIG. 8B) or a plurality of small streams (FIG. 8C). It is envisioned that each of the streams emanating from the above disclosed tips may be the same or different aerosolized solutions. Although shown as being adjustable, the tip may include only a single, fixed tip.

In some embodiments, portions of the surgical field may be lined with at least one mask made of an inert substance, such as silicone, to protect the portions of the surgical field from coming in contact with the aerosolized compositions. In embodiments, the mask may also be used to act as a mold or screen for collecting the aerosolized composition into a predetermined configuration, contour, and/or shape inside the surgical field.

The applicators described herein deliver the compositions and/or mixtures which include therapeutic agents, biocompatible carrier materials, and solvents in situ to form implantable films or therapeutic depots in any pattern, dimension, configuration deemed necessary by the medical personnel performing the surgery. In some instances the therapeutic agent and the carrier material may not be soluble in a common solvent or water-soluble.

The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic affect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anticonvulsants; antiemetics; antihistamines; anti-inflammatory agents, such as hormonal agents, hydrocortisone, prednisolone, prednisone, non-hormonal agents, allopurinol, indometachin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable therapeutic agents include, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

In some embodiments, the therapeutic agent may be a water-soluble drug. Some specific non-limiting examples of water-soluble drugs that may be used in the present polymeric films include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof In still other embodiments, the therapeutic agent may be a water insoluble drug such as bupivicaine in the free base form of bupivicaine.

In certain embodiments, the drug may not need to be converted to a salt form, i.e., tetracycline hydrochloride. In some embodiments, the therapeutic agent may include an anesthetic, i.e., bupivicaine, lidocaine, benzocaine, and the like.

In other embodiments, the therapeutic agent may a drug for treating cancer or for other oncology related treatments, such as 5-fluorouracil, methotrexate, cisplatin, daunorubucub, mitoxantrone, and carboplatin.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with a variety of different biocompatible carrier materials and solvents. The biocompatible carrier materials may be polymeric or non-polymeric.

The biocompatible material may be bioabsorbable or non-bioabsorbable. Some non-limiting examples of bioabsorbable materials include suitable polysaccharides such as cellulose, dextran, chitin, chitosan, alginate, pectin, mucilage, pullalan, methylcellulose, carboxymethylcullose, hydroxypropyl methylcellulose, hyaluronic acid (HA), hydroxyethyl methylcellulose, arabinoxylans, bacterial polysaccharides and combinations thereof.

Some additional non-limiting examples of bioabsorbable materials include polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ϵ-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; 6,8-dioxabicyclooctane-7-one; and polymer blends and copolymers thereof.

Other suitable bioabsorbable materials may include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; mucilage, pectin; and combinations thereof.

In embodiments, the biocompatible carrier material may be non-bioabsorbable. Suitable non-limiting examples of such materials include polypropylene, polyethylene terethphalate, polytetrafluoroethylene, and the like.

In still other embodiments, the biocompatible carrier material may be a non-polymeric material, which often may be insoluble in water and/or insoluble in an aqueous biologic system. Exemplary such non-polymeric carrier materials include, but are not limited to: sterols such as cholesterol, stigmasterol, β-sitosterol, and estradiol; cholestery esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof, sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Certain preferred non-polymeric carriers include cholesterol, glyceryl monostearate, glycerol tristearate, stearic acid, stearic anhydride, glyceryl monocleate, glyceryl monolinoleate, and acetylated monoglycerides.

The term "non-polymeric" may refer to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "nonpolymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein.

Many types of volatile organic solvents can also be combined with the therapeutic agents and biocompatible carriers to form the compositions described herein. Some non-limiting examples include ethers, esters, halogenated ethers, hydrocarbons, halohydrocarbons, or Freons, diethyl ether, chloroform, tetrahydrofuran, ethyl acetate, forane, and any combinations thereof are suitable for use in making the therapeutic compositions described herein.

It is envisioned that any combination of therapeutic agent, biocompatible carrier and solvent may be passed through the applicators described herein in situ to form a high payload therapeutic film or therapeutic depot. In embodiments the therapeutic agent may be kept separate from the carrier prior to passing through the applicator. In other embodiments, the therapeutic agent and carrier may be mixed in a common composition prior to passing through the applicator.

In particular embodiments, a composition which includes a therapeutic solution containing at least one water-soluble therapeutic agent and a polymer solution containing at least one hydrophobic polymer may be combined in a common solvent and passed through the applications described herein to form therapeutic film in situ capable of controlling and/or sustaining the release of the therapeutic agent post operatively. Alternatively, in some embodiments, the solvent for the therapeutic agent is not a co-solvent for the hydrophobic polymer. In some embodiments, the hydrophobic polymer is not miscible in the solvent for the therapeutic agent.

In certain embodiments, a water-soluble therapeutic agent may form a solution at a concentration ranging from about 1 microgram/ml to about 1 gram/ml. In certain embodiments, the concentration of the therapeutic solution may range from about 1 mg/ml to about 500 mg/ml. In still other embodiments, the concentration of the therapeutic solution may range from about 10 mg/ml to about 300 mg/ml. By solution, the therapeutic preparation is intended to include suspensions, emulsions, dispersions, and the like.

In a certain embodiment, a first hydrophobic polymer solution and a second water-soluble therapeutic solution may be provided. The first polymer solution contains 30 mg/ml poly(glycolide-co-caprolactone) dissolved in methylene chloride and is placed in a first reservoir of the applicator. The second therapeutic solution contains 100 mg/ml of bupivicaine dissolved in methanol and is placed in a second reservoir of the applicator. The applicator may be connected to a heated air flow source and includes an ultrasonic spray nozzle which the two solutions will pass through. The two solutions are kept separate from each other until atomized at the tip of the nozzle. The nozzle vibrates at a frequency of 48 kHz and is operated at 6 watts. The solutions are passed through the nozzle at a flow rate of about 1 ml/min while the nozzle is moving at a rate of 100 mm/sec at heights ranging from 30 mm to 60 mm. The atomized solutions form droplets that mix, either in the applicator and/or between the applicator and the tissue inside the surgical field, when the droplets fall from the tip of the nozzle. An air curtain kept at a pressure of 1.0 kPa surrounds the falling droplets. The droplets deposited onto the tissue are dried to for a single layer therapeutic film via the patient's natural body temperature and/or via the heated air flow which drives the mixture out of the applicator.

In another embodiment, the first polymer solution contains 30 mg/ml poly(glycolide-co-caprolactone) dissolved in methylene chloride and is placed in a first reservoir of the applicator. The second therapeutic solution contains 100 mg/ml of bupivicaine dissolved in methanol and is placed in a second reservoir of the applicator. The applicator may be connected to a heated air flow source and includes a first and second ultrasonic spray nozzle which the two solutions will pass through respectively. The two solutions are kept separate from each other until atomized at the tip of the nozzle. The nozzle vibrates at a frequency of 48 kHz and is operated at 6 watts. The solutions are passed through the nozzle at a flow rate of about 1 ml/min while the nozzle is moving at a rate of 100 mm/sec at heights ranging from 30 mm to 60 mm. The atomized solutions form droplets that mix, either in the applicator and/or between the applicator and the tissue inside the surgical field, when the droplets fall from the tip of the nozzle. An air curtain kept at a pressure of 1.0 kPa surrounds the falling droplets. The first polymer solution is passed through the first spray nozzle to form droplets that are deposited onto the tissue, an implanted medical device, or both, to form a first polymer layer. The thickness of the polymer layer may be controlled by the number of applications of the coating solution. The first polymer solution and the second therapeutic solution are then passed through the first and second spray nozzles, respectively, to form droplets which mix when the droplets fall from the tip of the nozzle onto the first polymer layer previously formed on the sheet of silicone. This forms a second layer which includes both the polymer and therapeutic agent. Then the first polymer solution is passed through the first spray nozzle again while the flow rate of the second therapeutic solution is stopped. Droplets of the first polymer solution are formed and deposited onto the second layer previously formed on top of the first layer and are dried to form a tri-layer structure via the patient's natural body temperature and/or via the heated air flow which drives the mixture out of the applicator. In some instances, the tri-layer structure may be exposed to increased heat and compression to dry and join the tri-layer structure.

In still other embodiments, a therapeutic film may be formed by using a 2-step process. In the first step, a first therapeutic aqueous composition and a lipid containing composition may be passed through an ultrasonic sprayer to produce a water-in-oil emulsion. In the second step, the water-in-oil emulsion is then dispersed into a second aqueous phase and passed through an ultrasonic sprayer to from the therapeutic films described herein.

The first therapeutic composition includes a therapeutic agent, such as an anesthetic, at least one polyhydroxy carboxylic acid, and at least one di- or tri-protic mineral acid. Examples of suitable di- or tri-protic mineral acids include sulfuric acid, and phosphoric acid. Examples of polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

In such embodiments, the lipid composition is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes. Suitable amphipathic lipids are zwitterionic phospholipids, including phosphatidylcholine, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamine. Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

In yet other embodiments, a therapeutic film as described herein may be formed by passing a composition which includes a therapeutic agent, a non-polymeric carrier and a solvent, wherein the solvent may or may not be another therapeutic agent. For example, an anesthetic, such as bupivicaine (free base), may be combined with a non-polymeric carrier such as sucrose acetate isobutyrate in N-methylpyrrolidone or benzoyl alcohol. This composition as a single mixture may be passed through the applicators described herein in situ to form any number of layers of a therapeutic depot or film.

A number of suitable additives may be included with the composition in order to impart selected characteristics upon the composition. For example, the may include a minor amount of a biodegradable thermoplastic polymer such as a polylactide, polycaprolactone, polyglycolide, or copolymer thereof. Optionally, a pore-forming agent can be included in the composition. The pore-forming agent can be any organic or inorganic, pharmaceutically-acceptable substance that is substantially soluble in water or body fluid, and will dissipate from the non-polymeric carrier material and/or the solid matrix of an implant into surrounding body fluid at the implant site. The pore-forming agent may preferably be insoluble in the organic solvent to form a uniform mixture with the non-polymeric carrier material. The pore-forming agent may also be a water-immiscible substance that rapidly degrades to a water-soluble substance. In certain compositions, the pore-forming agent is combined with the non-polymeric carrier and organic solvent in admixture. Suitable pore-forming agents that can be used in the composition include, for example, sugars such as sucrose and dextrose, salts such as sodium chloride and sodium carbonate, polymers such as hydroxylpropylcellulose, carboxymethylcellulose, polyethylene glycol and polyvinylpyrrolidone, and the like. Solid crystals that will provide a defined pore size, such as salt or sugar, are preferred.

In still other embodiments, a therapeutic solution including bupivicaine free base suspended in a solution alone or with any of the following: a biopolymer, such as collagen, oxidized collagen, hyaluronic acid, elastin, keratin, and the like; other polymer carriers including polyethylene glycol, lactones, polysaccharides, and the like; pre-polymerized gels including PEG succidimidyl esters or polyurethanes, may be passed through the applicators described herein to form therapeutic films in situ.

In yet another embodiment, an anesthetic such as free base bupivicaine may be micronized in combination with lactone particles or other milled polymeric materials such as dried crosslinked collagen prior to forming a solution or suspension and being passed through the applicators described herein to form therapeutic films in situ.

The use of free base bupivicaine may increase the residence time and sustained release of the therapeutic agent when implanted.

The systems, compounds, and methods disclosed herein may also find application in robotic surgery. For example, the system may be adapted for use on the da Vinci Robotic Surgery System by Intuitive Surgical, Inc.

One method of using the systems, compounds, and methods disclosed herein is to use the system to apply the compounds disclosed herein immediately upon accessing the surgical site prior to internal tissue manipulation. Such application may have the desirable effect of reducing pain and tissue trauma both during and after the surgical procedure. In another method of using the systems, compounds, and methods disclosed herein is to apply the compounds disclosed herein to the surgical site at the completion of the surgery, just prior to closure of the surgical access incision. Such application may have the desirable effect of reducing negative post-operative issues such as pain.

It will be understood that various modifications may be made to the embodiments disclosed herein. For example, in embodiments the therapeutic films may be deposited directly on a surgical mesh to not only provide a therapeutic effect but may also assist with anchoring the mesh in place. Thus, those skilled in the art will envision other modifications within the scope and spirit of the claims.

What is claimed is:

1. An applicator for use in surgical procedures comprising:
- a base including a proximal and distal ends and defining an elongated passage extending therebetween,
- a reservoir for receiving a composition,
- a mechanism for aerosolizing the composition, the mechanism positioned between the reservoir and the base, and,
- a polymerizing member positioned within the base on a length of the elongated passage, wherein the polymerizing member is configured to polymerize the composition as the composition passes through the applicator and the polymerizing member comprises at least one of an ultraviolet light emitting diode, infrared light emitting diode, ultraviolet bulb, infrared bulb, or microwave generator.

2. The applicator of claim 1 wherein the base comprises a rigid material.

3. The applicator of claim 1 wherein the base comprises a flexible material.

4. The applicator of claim 1 wherein the base comprises perforations.

5. The applicator of claim 1 further comprising more than one reservoir.

6. The applicator of claim 1 further comprising more than one mechanism for aerosolizing the composition.

7. The applicator of claim 1 wherein the mechanism for aerosolizing comprises a nebulizer.

8. The applicator of claim 1 wherein the mechanism for aerosolizing comprises an ultra-sonic sprayer.

9. The applicator of claim 1 wherein the polymerizing member comprises a light emitting diode or bulb.

10. The applicator of claim 1 wherein the polymerizing member comprises a microwave generator.

11. The applicator of claim 1 further comprising an adjustable tip positioned on the distal end of the base.

12. The applicator of claim 11 wherein the air source is heated.

13. The applicator of claim 1 further comprising an air source positioned on the proximal end of the base.

14. The applicator of claim 1 wherein the polymerizing member is positioned on the distal end of the base.

15. A method of forming implantable therapeutic films in situ comprising:
- positioning an applicator at a surgical site, the applicator including a base including a proximal and distal ends and defining an elongated passage extending therebetween, a reservoir for receiving a composition, a mechanism for aerosolizing the composition, the mechanism positioned between the reservoir and the base, and, a polymerizing member positioned within the base on a length of the elongated passage, wherein the polymerizing member is configured to polymerize the composition as the composition passes through the applicator and the polymerizing member comprises at least one of an ultraviolet light emitting diode, infrared light emitting diode, ultraviolet bulb, infrared bulb, or microwave generator, and,
- passing the composition through the applicator to form an implantable therapeutic film in situ, the composition including, individually or in any combination, a therapeutic agent, a biocompatible carrier and a solvent.

16. The method of claim 15 wherein the applicator is positioned at a surgical site via a laparoscopic procedure.

17. The method of claim 15 wherein the applicator is positioned at a surgical site via an open procedure.

18. The method of claim 15 wherein the passing of the composition occurs after accessing the surgical site and prior to internal tissue manipulation.

19. The method of claim 15 wherein the passing of the composition occurs at the completion of the surgery and prior to closure of the surgical site.

20. An applicator for use in surgical procedures comprising:
   a base including a proximal and distal ends and defining an elongated passage extending therebetween,
   a reservoir for receiving a composition,
   a mechanism for aerosolizing the composition, the mechanism positioned between the reservoir and the base, and,
   a polymerizing member positioned within the base on a length of the elongated passage, wherein the polymerizing member polymerizes the composition as the composition passes through the elongated passage of the base and prior to being dispensed through an outlet in the elongated passage and the polymerizing member comprises at least one of an ultraviolet light emitting diode, infrared light emitting diode, ultraviolet bulb, infrared bulb, or microwave generator.

* * * * *